(12) United States Patent
Umezawa et al.

(10) Patent No.: US 8,742,699 B2
(45) Date of Patent: Jun. 3, 2014

(54) CHARGED PARTICLE BEAM GENERATOR, CHARGED PARTICLE IRRADIATION SYSTEM, METHOD FOR OPERATING CHARGED PARTICLE BEAM GENERATOR AND METHOD FOR OPERATING CHARGED PARTICLE IRRADIATION SYSTEM

(75) Inventors: Masumi Umezawa, Mito (JP); Yoshifumi Hojo, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 324 days.

(21) Appl. No.: 13/095,470

(22) Filed: Apr. 27, 2011

(65) Prior Publication Data

US 2011/0266981 A1 Nov. 3, 2011

(30) Foreign Application Priority Data

Apr. 30, 2010 (JP) ................. 2010-105522

(51) Int. Cl.
*H05H 7/02* (2006.01)

(52) U.S. Cl.
USPC ............................. 315/506; 315/500; 315/505

(58) Field of Classification Search
USPC .......................................... 315/506, 500, 505
See application file for complete search history.

(56) References Cited

U.S. PATENT DOCUMENTS

| | | | |
|---|---|---|---|
| 5,969,367 | A | 10/1999 | Hiramoto et al. |
| 7,554,275 | B2 * | 6/2009 | Amaldi ........................ 315/505 |
| 7,838,855 | B2 | 11/2010 | Fujii et al. |
| 8,227,775 | B2 | 7/2012 | Saito et al. |
| 2005/0116175 | A1 | 6/2005 | Haberer |
| 2008/0237494 | A1 | 10/2008 | Beloussov et al. |
| 2009/0283702 | A1 * | 11/2009 | Umezawa et al. ......... 250/492.3 |

FOREIGN PATENT DOCUMENTS

| | | |
|---|---|---|
| EP | 0 779 081 A2 | 6/1997 |
| JP | 2833602 B2 | 12/1998 |
| JP | 2001-326098 A | 11/2001 |
| JP | 3518270 B2 | 4/2004 |
| JP | 2007-42659 A | 2/2007 |
| JP | 2009-347 A | 1/2009 |
| JP | 2009-112483 A | 5/2009 |
| WO | WO 03/069634 A2 | 8/2003 |

OTHER PUBLICATIONS

Kenji Sawada, et al. "Design, Manufacture, and Performance Test of the Injector for Hyogo Hadrontherapy Center", Proc. of the 12th Symposium on Accelerator Science and Technology, Wako, Japan 1999, pp. 367-369.

(Continued)

*Primary Examiner* — Alexander H Taningco
*Assistant Examiner* — David Lotter
(74) *Attorney, Agent, or Firm* — Crowell & Moring LLP

(57) ABSTRACT

A charged particle beam generator, a charged particle irradiation system, a method for operating the charged particle beam generator and a method for operating the charged particle irradiation system, which allow a charged particle beam to be injected into a circular accelerator at an arbitrary timing and can reduce an irradiation time and a time for a therapy, are provided while maintaining the lower limit of an operation cycle of a linear accelerator. An accelerator control device controls an operation of a synchrotron on the basis of a beam extraction request signal transmitted from a beam utilization system control device. A control device generates a timing signal notifying the linear accelerator of an injection timing of a next operation cycle of the synchrotron after completion of an extraction process performed by the synchrotron, changes an operation timing of the linear accelerator so that the operation timing of the linear accelerator matches the injection timing.

19 Claims, 12 Drawing Sheets

(56) References Cited

OTHER PUBLICATIONS

M. Maier, et al. "Commissioning of the Linac for the Heidelberg Heavy Ion Cancer Therapy Centre (Hit)", Proceedings of Particle Accelerator Conference 2007. pp. 2734-2736.

Akira Takagi, Oho' 96 High Energy Accelerator Seminar, High-intensity Proton Accelerator of Hadron Project 1996, pp. I-17 & I-18.
Japanese Office Action dated Aug. 20, 2013 (Two (2) pages).
European Search Report dated Mar. 19, 2014 (Nine (9) pages).

* cited by examiner

FIG. 6

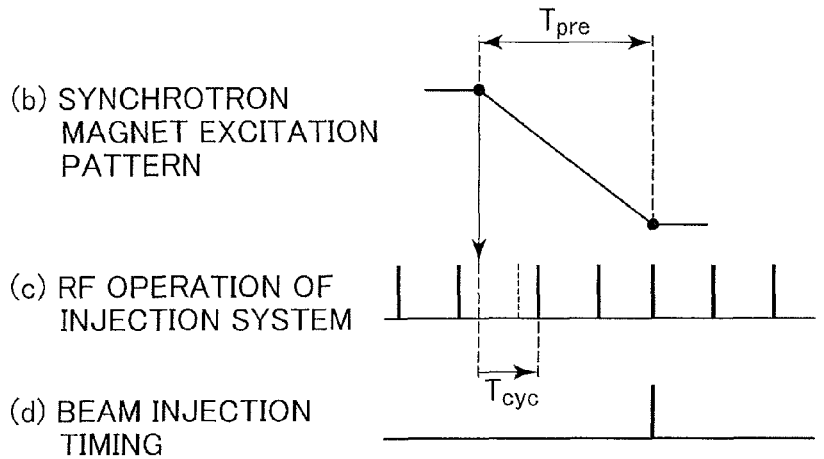

(b) SYNCHROTRON MAGNET EXCITATION PATTERN (c) RF OPERATION OF INJECTION SYSTEM (d) BEAM INJECTION TIMING $T_{pre} = N \times T_{cyc}$ (N IS INTEGER)
EXAMPLE IN WHICH N = 3

FIG. 7

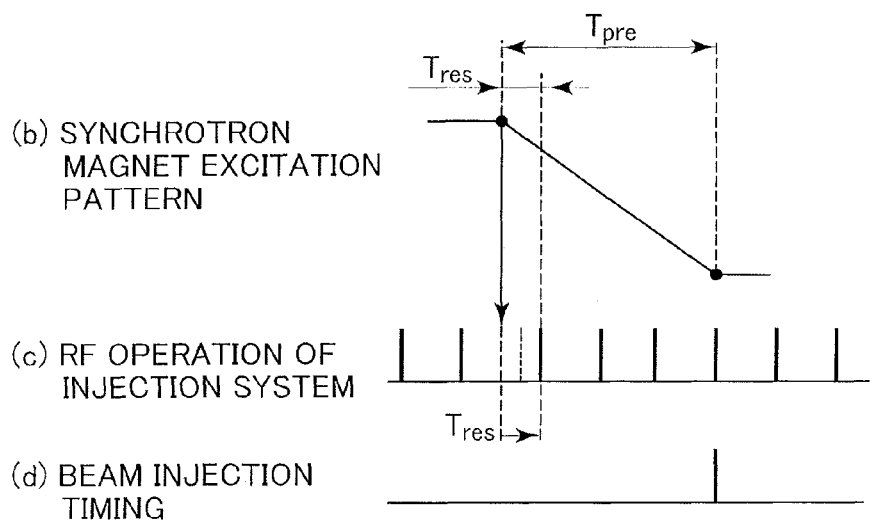

(b) SYNCHROTRON MAGNET EXCITATION PATTERN (c) RF OPERATION OF INJECTION SYSTEM (d) BEAM INJECTION TIMING $T_{pre} = M \times T_{cyc} + T_{res}$ (M IS INTEGER)
EXAMPLE IN WHICH M = 3
WHEN SUM OF $T_{res}$ AND TIME THAT ELAPSES FROM RF OPERATION TIMING IMMEDIATELY BEFORE GENERATION OF INJECTION PRETRIGGER SIGNAL IS LARGER THAN $T_{cyc}$, RF OPERATION TIMING IS GENERATED WHEN $T_{res}$ ELAPSES AFTER GENERATION OF INJECTION PRETRIGGER SIGNAL

FIG. 8

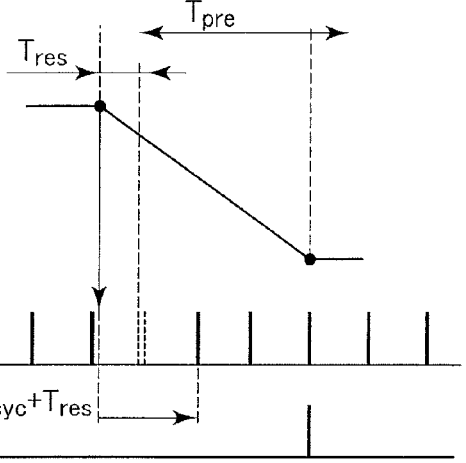

(b) SYNCHROTRON MAGNET EXCITATION PATTERN (c) RF OPERATION OF INJECTION SYSTEM (d) BEAM INJECTION TIMING $T_{pre} = M \times T_{cyc} + T_{res}$ (M IS INTEGER)
EXAMPLE IN WHICH M = 3
WHEN SUM OF $T_{res}$ AND TIME THAT ELAPSES FROM RF OPERATION TIMING IMMEDIATELY BEFORE GENERATION OF INJECTION PRETRIGGER SIGNAL IS SMALLER THAN $T_{cyc}$, RF OPERATION TIMING IS GENERATED WHEN $T_{cyc}$ AND $T_{res}$ ELAPSE AFTER GENERATION OF INJECTION PRETRIGGER SIGNAL

FIG. 9

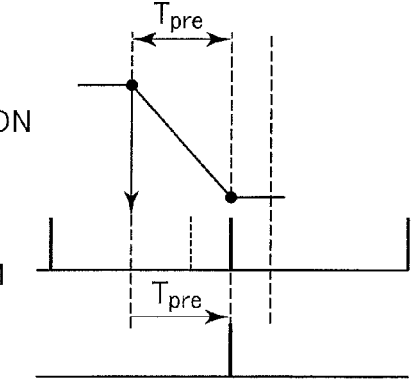

(b) SYNCHROTRON MAGNET EXCITATION PATTERN (c) RF OPERATION OF INJECTION SYSTEM (d) BEAM INJECTION TIMING

EXAMPLE IN WHICH $T_{cyc} > T_{res}$
WHEN SUM OF $T_{pre}$ AND TIME THAT ELAPSES FROM RF OPERATION TIMING IMMEDIATELY BEFORE GENERATION OF INJECTION PRETRIGGER SIGNAL IS LARGER THAN $T_{cyc}$, RF OPERATION TIMING IS GENERATED WHEN $T_{pre}$ ELAPSES AFTER GENERATION OF INJECTION PRETRIGGER SIGNAL

CHARGED PARTICLE BEAM GENERATOR, CHARGED PARTICLE IRRADIATION SYSTEM, METHOD FOR OPERATING CHARGED PARTICLE BEAM GENERATOR AND METHOD FOR OPERATING CHARGED PARTICLE IRRADIATION SYSTEM

BACKGROUND OF THE INVENTION

1. Field of the Invention

The present invention relates to a charged particle beam generator, a charged particle irradiation system, a method for operating the charged particle beam generator and a method for operating the charged particle irradiation system. The invention more particularly relates to a charged particle beam generator provided with a circular accelerator and an injection linear accelerator, a method for operating the charged particle beam generator provided with the circular accelerator and the injection linear accelerator, a charged particle irradiation system that is provided with an irradiation device for irradiating a tumor (target to be irradiated) such as a tumor with a charged particle beam extracted from a charged particle beam generator and cures the tumor through the irradiation with the charged particle beam, and a method for operating the charged particle irradiation system provided with the irradiation device.

2. Description of the Related Art

A linear accelerator for injection is provided for a circular accelerator such as a synchrotron and located on the upstream side of the circular accelerator. The linear accelerator accelerates charged particles generated by an ion source until the charged particles have predetermined energy appropriate for injection into the circular accelerator. Then, the circular accelerator which has received the charged particle further accelerates the charged particles until the charged particles have higher energy. The thus-accelerated charged particles are used for particle beam therapy with which a patient is cured by irradiating the tumor (such as cancers) of the patient with charged particle beams.

A radio frequency voltage is conventionally used to accelerate the injection linear accelerator provided for the circular accelerator for particle beam therapy. The injection linear accelerator includes an RF power supply device for generating radio frequency voltages. Also, an ion source used for generating charged particles needs a radio frequency voltage for ion generation and includes another RF power supply device for generating radio frequency voltages. With this, the operation cycle of the linear accelerator is determined by that of the RF power supply device. The minimum operation cycle of the linear accelerator is 0.5 seconds or a frequency of 2 Hz (Non-Patent Document 1 (Kenji SAWADA, et al. "Design, Manufacture, and Performance Test of the Injector for Hyogo Hadrontherapy Center" Proc. of The 12th Symposium on Accelerator Science and Technology, Wako Japan 1999), 367 page) or 0.2 seconds or a frequency of 5 Hz (Non-Patent Document 2 (M. Maier et. al "Commissioning of the Linac for the Heidelberg Heavy Ion Center Therapy Center (HIT)" Proc. of Particle Accelerator Conference 2007), page 2734).

The operation cycle of the linear accelerator is fixed, or the minimum operation cycle of the linear accelerator is limited. This is due to the fact that when the operation cycles of the RF power supply devices are increased to a value that is three or four times the fixed cycle or minimum cycle, the operations or radiofrequency characteristics of the RF power supply devices depart from stationary operations, become unstable and affect characteristics of the beam. Further, this is due to the fact that when the operation cycles of the RF power supply devices are reduced to a fraction of the fixed cycle or minimum cycle, thermal loads or the like of the RF power supply devices or thermal loads or the like of radiofrequency devices are increased and the operations of the devices become unstable and affect the characteristics of the beam. Thermal loads resulting from reduction in the operation cycles may bring about a failure in devices due to their heat. Thus, for the purpose of device protection, the time (operation cycle) it takes from operation to operation is made longer. That is, the minimum operation cycle needs to be limited.

There is a method of supplying a charged particle beam from a beam injection device at desired timings when RF power supplies in a linear accelerator provided for acceleration and an ion source operates in a fixed cycle or a substantially fixed cycle. Such a method is known in Non-Patent Document 3 (Akira Takagi OHO' 96 High Energy Accelerator Seminar, High-intensity proton accelerator of Hadron Project 1996, pages I-17, 18). Specifically Non-Patent Document 3 describes a method for adding a delay time (sufficiently smaller than the operation cycle) to one of the two timings such that charged particles are prevented from being accelerated when they are not necessary, and for accelerating the charged particle beams only when they are necessary while the frequency voltage for acceleration is matched with the frequency voltage for the ion source without the addition of the delay time.

When the charged particle beam accelerated by the circular accelerator is used for particle beam therapy, the heart rate or respiration of the patient may move his or her tumor from a set position. To cope with this, the circular accelerator is controlled such that the charged particle beam is extracted only when the tumor is located in place (See Japanese Patent No. 3518270). However, when charged particle beams are to be injected into the circular accelerator at a timing as described in Japanese Patent No. 3518270, the operation cycle of the beam injection device (injection accelerator) is fixed or the minimum operation cycle of the beam injection device is limited in some cases. In such a case, a waiting time, i.e., a time period corresponding to one operation cycle of the beam injection device is required at maximum based on the time when the charged particle beams are to be injected. As a result, it is considered that the circular accelerator cannot be operated as desired and irradiation time is increased by a time period corresponding to the waiting time; accordingly a burden on the patient may be further added.

In addition, Japanese Patent Nos. 3518270 and 2833602 describe an irradiation method in which when the charged particle beam accelerated by the circular accelerator is used for particle beam therapy, tumor irradiation is performed as follows. The tumor is divided into layers in a depth direction and the charged particle beam is scanned across each of the layers in alignment with the tumor shape. After the irradiation of the layer is completed, the tumor is irradiated while the energy of the charged particle beam extracted from the circular accelerator is changed. As shown in FIG. 8 of Japanese Patent No. 2833602, when the circular accelerator is to change a layer to be irradiated, a beam extraction signal is transmitted to the injection accelerator for acceleration of charged particles. However, the operation cycle of the injection accelerator is fixed or the minimum operation cycle of the injection accelerator is limited in some cases. In such a case, a waiting time, i.e., a time period corresponding to one operation cycle of the beam injection device is required at maximum based on the time when the charged particle beams are to be injected. As a result, it is considered that the circular accelerator cannot be operated as desired and irradiation time is increased by a time period corresponding to the waiting time; accordingly a burden on the patient may be further added.

SUMMARY OF THE INVENTION

As described above, since the operation cycle of the conventional injection linear accelerator is fixed or the minimum operation cycle of the conventional injection linear accelerator is limited, a waiting time, i.e., a time period corresponding to one operation cycle of the linear accelerator is necessary before a beam injection timing requested from the circular accelerator. When the high-energy charged particle beam formed by the circular accelerator is used for particle beam therapy, the operation of the circular accelerator is limited in that the circular accelerator operates in synchronization with the patient's movement or the circular accelerator operates such that irradiation is performed with the tumor divided into a plurality of layers or regions. In addition, the time it takes to irradiate the patient is increased and a burden on the patient is further added, leading to a reduction in the number of patients to be cured per unit time in curing equipment. In order to utilize the beam at an optional timing in the injection linear accelerator, it is necessary that the operation cycle of the linear accelerator be variable or the operational times or operation cycles of the RF power supply devices be reduced. If such measures are taken, however, the linear accelerator will become unstable in operation and beam characteristics. Further, thermal loads attributable to the RF power supply devices or the radiofrequency device may cause devices to abnormally operate. As a result, it is disadvantageously requested to improve performance of the RF power supply devices and increase the size of the linear accelerator.

An object of the present invention is to provide a charged particle beam generator, a charged particle irradiation system, a method for operating the charged particle beam generator and a method for operating the charged particle irradiation system, which allow a charged particle beam to be injected into a circular accelerator at an arbitrary timing and can reduce an irradiation time and a time for therapy while maintaining a lower limit of an operation cycle of a linear accelerator.

In order to accomplish the aforementioned object, in an operation cycle (of the circular accelerator) including a process of injection, acceleration, extraction, and deceleration, an operation timing of the linear accelerator is changed after completion of the process of causing the charged particle beam to be extracted from the circular accelerator so that the operation cycle of the linear accelerator temporarily increases and the operation timing of the linear accelerator matches an injection timing of the next operation cycle of the circular accelerator. A pretrigger timing signal that notifies the linear accelerator of a requested injection timing after completion of the extraction process is provided for timing control in order to control the injection, acceleration, extraction, and deceleration processes of the circular accelerator.

Thus, the charged particle beam can be injected into the circular accelerator at an arbitrary timing while the lower limit of the operation cycle of the linear accelerator is maintained. In other words, the charged particle beam can be injected into the circular accelerator at an injection timing requested by the circular accelerator without a reduction in the operation cycle of the linear accelerator or a reduction in a time interval between pulses generated by an RF power supply included in the linear accelerator.

According to the present invention, the charged particle beam can be injected at an arbitrary timing into the circular accelerator that uses the injection linear accelerator that operates in an operation cycle. The minimum operation cycle of the injection linear accelerator is limited. Thus, the charged particle beam can be injected into the circular accelerator at the injection timing requested by the circular accelerator without a reduction in the operation cycle of the linear accelerator. As a result, the time it takes to irradiate the patient can be reduced and a time period for therapy can be reduced in the charged particle beam irradiation device that utilizes the charged particle beam accelerated by the circular accelerator, and the system can efficiently operate.

BRIEF DESCRIPTION OF THE DRAWINGS

FIG. 6 is a timing chart of an example of operations of the charged particle beam irradiation system according to the first embodiment of the invention.

FIG. 7 is a timing chart of another example of the operations of the charged particle beam irradiation system according to the first embodiment of the invention.

FIG. 8 is a timing chart of another example of the operations of the charged particle beam irradiation system according to the first embodiment of the invention.

FIG. 9 is a timing chart of another example of the operations of the charged particle beam irradiation system according to the first embodiment of the invention.

DESCRIPTION OF THE PREFERRED EMBODIMENTS

Preferred embodiments of the invention are described below with reference to the accompanying drawings.

First Embodiment

Figure 1:
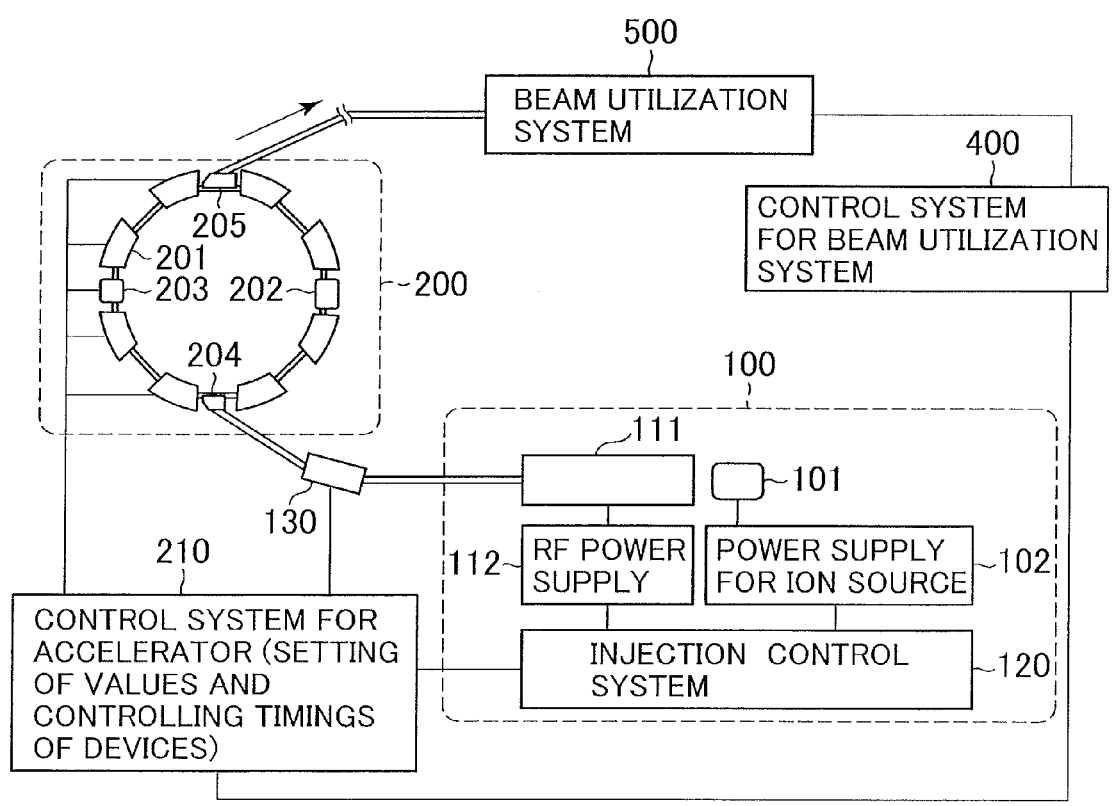
FIG. 1 is an outline diagram showing the entire configuration of a charged particle beam irradiation system according to a first embodiment of the invention.

FIG. 1 is an outline diagram showing the entire configuration of a charged particle beam irradiation system according to a first embodiment of the invention.

The charged particle beam irradiation system according to the first embodiment includes an injection system 100, an injection beam transport system 130, a synchrotron (circular accelerator) 200, a beam utilization system 500, an accelerator control device (control device or second control device) 210 and a beam utilization system control device (first control device) 400. The injection system 100 generates a charged particle beam and accelerates the charged particle beam so that the charged particle beam has energy that is necessary for the beam to be injected into the synchrotron 200. The injection beam transport system 130 transports the charged particle beam generated by the injection system 100 to the synchrotron 200. The synchrotron 200 accelerates the injected charged particle beam so that the charged particle beam has desired energy. The beam utilization system 500 utilizes the charged particle beam accelerated by the synchrotron 200.

The injection system 100 includes an ion source 101 that generates charged particles, a power supply 102 for the ion source 101, a linear accelerator 111 that accelerates the generated charged particles, an RF power supply 112 that generates a pulse voltage for the acceleration of the charged particles, and an injection control system 120. The synchrotron 200 includes a bending magnet 201, an RF acceleration cavity 202, beam extraction devices 203, 205, and a beam injection device 204 that is used for the injection of the beam. The injection system 100 and the synchrotron 200 are controlled by the accelerator control device 210. The injection system 100 and the synchrotron 200 operate on the basis of a beam extraction request signal, a next pattern transition request signal, an energy switch request signal and the like. The beam extraction request signal is transmitted from the control device 400 that controls the beam utilization system 500. The next pattern transition request signal is used to request a transition of an operational pattern of the synchrotron. The energy switch request signal is used to change energy of the beam to be extracted from the synchrotron 200. The injection system 100, the synchrotron 200 and the accelerator control device 210 form a charged particle beam generator.

Figure 2:
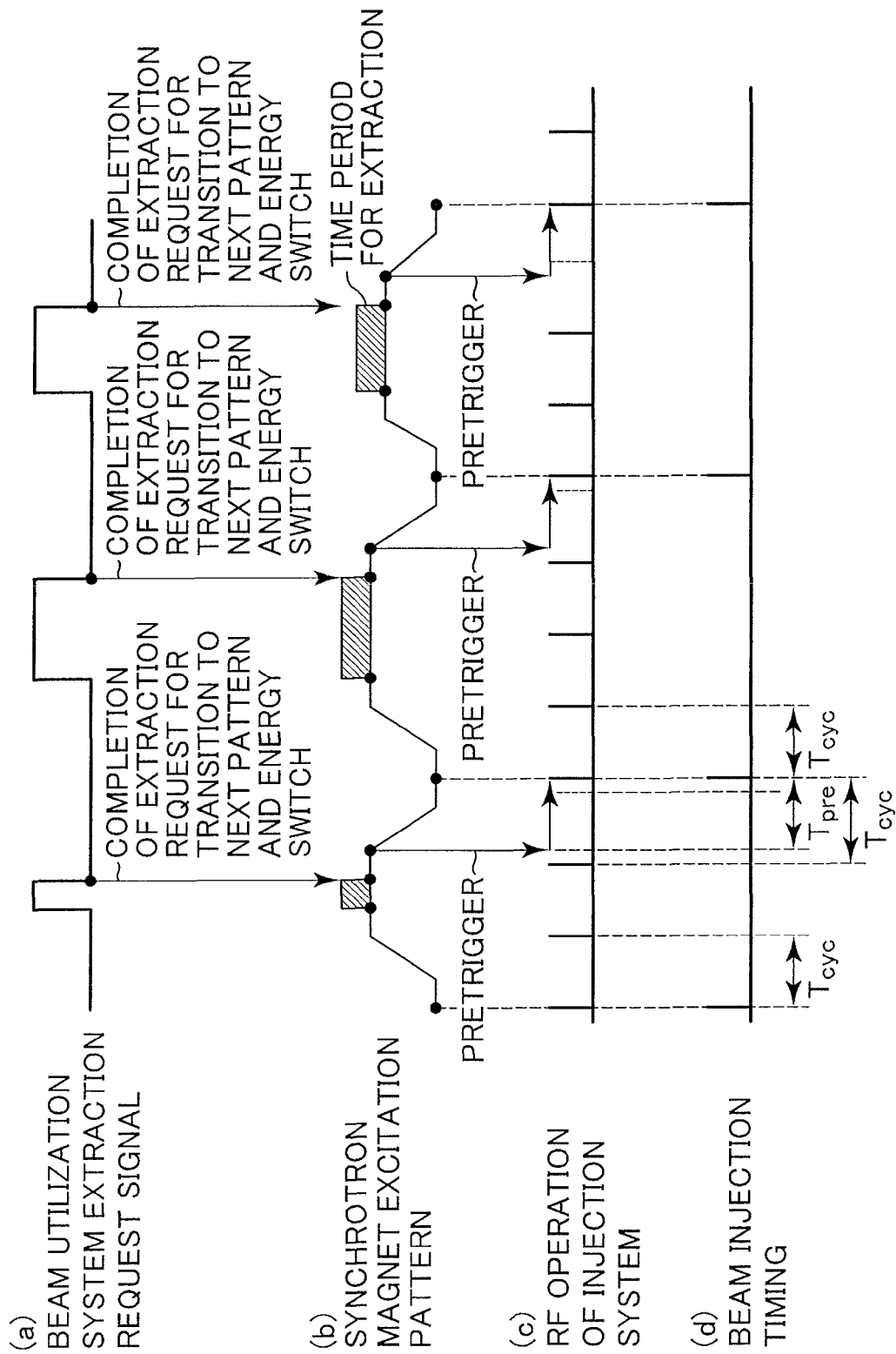
FIG. 2 is a timing chart of an example of operations of the charged particle beam irradiation system according to the first embodiment of the invention.

FIG. 2 is a timing chart of typical operations. A symbol (a) shown in FIG. 2 indicates a beam utilization system extraction request signal that is generated from the beam utilization system control device 400 and used to request a charged particle beam that satisfies conditions necessary for the beam utilization system 500. A symbol (b) shown in FIG. 2 indicates an excitation pattern of the bending magnet 201 as a representative example of a magnet excitation pattern that is an operational pattern of the synchrotron 200. The excitation pattern includes an injection process, an acceleration process, an extraction process and a deceleration process. The synchrotron 200 operates in an operation cycle that includes time periods for the processes.

Figure 3:
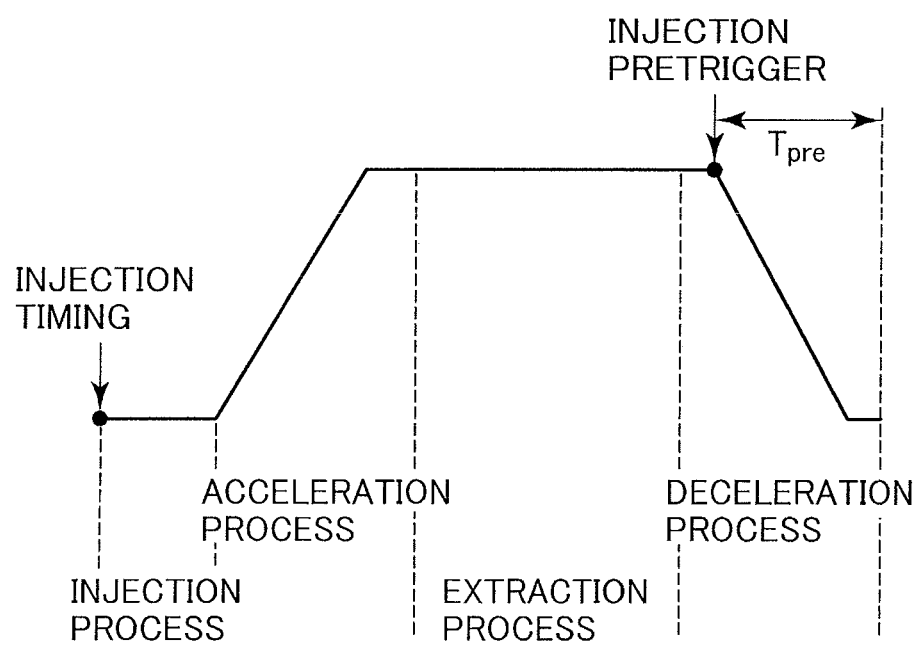
FIG. 3 is a diagram showing in detail an operational pattern of a synchrotron included in the charged particle beam irradiation system according to the first embodiment of the invention.

FIG. 3 shows details of the magnet excitation pattern of the synchrotron. In FIG. 3, an injection timing is the time when the charged particle beam accelerated by the linear accelerator 111 is injected into the synchrotron 200. The magnet excitation pattern is synchronized with control of corresponding radio frequency acceleration and radio frequency deceleration for a time period from the injection timing through the injection process and the acceleration process to the start of the extraction process and for a time period from the completion of the extraction process through the deceleration process to the injection timing of the next operation cycle of the synchrotron 200. The injection timing, operational patterns in the injection process, the acceleration process and the deceleration process, and time periods for the injection process, the acceleration process and the deceleration process are determined before the magnet excitation pattern is created.

A radio frequency operation of the linear accelerator 111 is performed in cycles (operation cycles indicated by $T_{cyc}$) indicated by a symbol (c) shown in FIG. 2. As indicated by the symbol (c) of FIG. 2, "radio frequency operation of beam injection device" means a radio frequency operation cycle of the linear accelerator 111. In the following description, the "radio frequency operation of the beam injection device" also indicates the same meaning. When the operation cycle of the synchrotron 200 is equal to an operation cycle $T_{cyc}$ of the beam injection device or equal to an integral multiple of the operation cycle $T_{cyc}$ of the beam injection device, the injection timing of the synchrotron 200 matches the time (operation timing of the linear accelerator 111) when the beam can be supplied from the linear accelerator 111, and the beam can be injected without a problem. When the time period for which the extraction request signal is transmitted from the beam utilization system 500 is not constant as indicated by the symbol (a) of FIG. 2, or when the time period for which the extraction request signal is transmitted from the beam utilization system 500 is constant and the operation cycle of the synchrotron 200 is not equal to the integral multiple of the operation cycle $T_{cyc}$ of the beam injection device, the injection timing does not match the operation cycle of the beam injection device and the synchrotron 200 waits for the injection of the beam for a certain time (waiting time). For an operation of the synchrotron 200, it is necessary to match the injection timing with the operation cycle of the beam injection device.

In the present embodiment, however, during the operation of the synchrotron 200, an injection pretrigger signal is generated at a specific time after completion of the extraction process so as to notify the injection system 100 of timing of injection of the beam in the next operation cycle of the synchrotron 200. Then, the timing of the radio frequency operation of the linear accelerator 111 is changed on the basis of the injection pretrigger signal so that the operation cycle of the beam injection device temporarily increases and the injection timing of the synchrotron 200 matches the time (operation timing of the linear accelerator 111) when the beam can be supplied from the linear accelerator 111. A symbol (d) shown in FIG. 2 indicates timings of injections of the beam. The generation timing of the injection pretrigger signal is set in a time period (shown in FIG. 3) that ranges from the time of completion of the extraction process to the time of termination of the deceleration process and is included in a time period ranging from the time of the completion of the extraction process to the injection timing of the next operation cycle of the synchrotron 200.

A time period that ranges from the time when the injection pretrigger signal is generated during the operation of the synchrotron 200 to the injection timing of the next operation cycle of the synchrotron 200 is indicated by $T_{pre}$ as shown in FIG. 2. The generation timing of the injection pretrigger signal is set to the time that is earlier by the time period $T_{pre}$ than the injection timing (known timing) of the next operation cycle of the synchrotron 200. In the example shown in FIG. 2, the operation cycle $T_{cyc}$ of the linear accelerator 111 is equal to the time period $T_{pre}$ that ranges from the generation time of the injection pretrigger signal to the injection time of the beam, or $T_{cyc}=T_{pre}$. When $T_{cyc}=T_{pre}$, a new cycle of the radio frequency operation of the beam injection device starts on the basis of the generation time of the injection pretrigger signal. Specifically, a radio frequency operation timing signal is generated for the linear accelerator 111 when the operation cycle $T_{cyc}$ of the linear accelerator 111 elapses after the generation time of the injection pretrigger signal. In this case, an actual operation cycle (indicated by $T'_{cyc}$) of the linear accelerator 111 temporarily increases and matches the injection timing of the synchrotron 200 without a reduction in the operation cycle of the beam injection device, and the beam can be supplied from the linear accelerator 111.

In this operating method, the increased operation cycle $T'_{cyc}$ does not exceed the double of the original basic cycle $T_{cyc}$, or $T'_{cyc} < 2 \cdot T_{cyc}$. Thus, the increased operation cycle $T'_{cyc}$ is not significantly changed from the basic cycle, and a stable operation can be performed.

The accelerator control device 210 forms a first control device that controls the beam extraction devices 203 and 205 of the synchrotron 200 in the process for causing the charged particle beam to be extracted from the synchrotron 200 in the operation cycle of the synchrotron 200 so that the charged particle beam is extracted only for a time period requested by the beam utilization system 500 (irradiation device). In addition, the accelerator control device 210 forms a second control device that changes the operation timing of the linear accelerator 111 after the process for extracting the charged particle beam from the synchrotron 200 is completed by the control of the beam extraction devices 203 and 205 in the operation cycle of the synchrotron 200 so that the operation cycle of the linear accelerator 111 temporarily increases, the second control device allowing the operation timing of the linear accelerator 111 to match the injection timing of the next operation cycle of the synchrotron 200.

Figure 4:
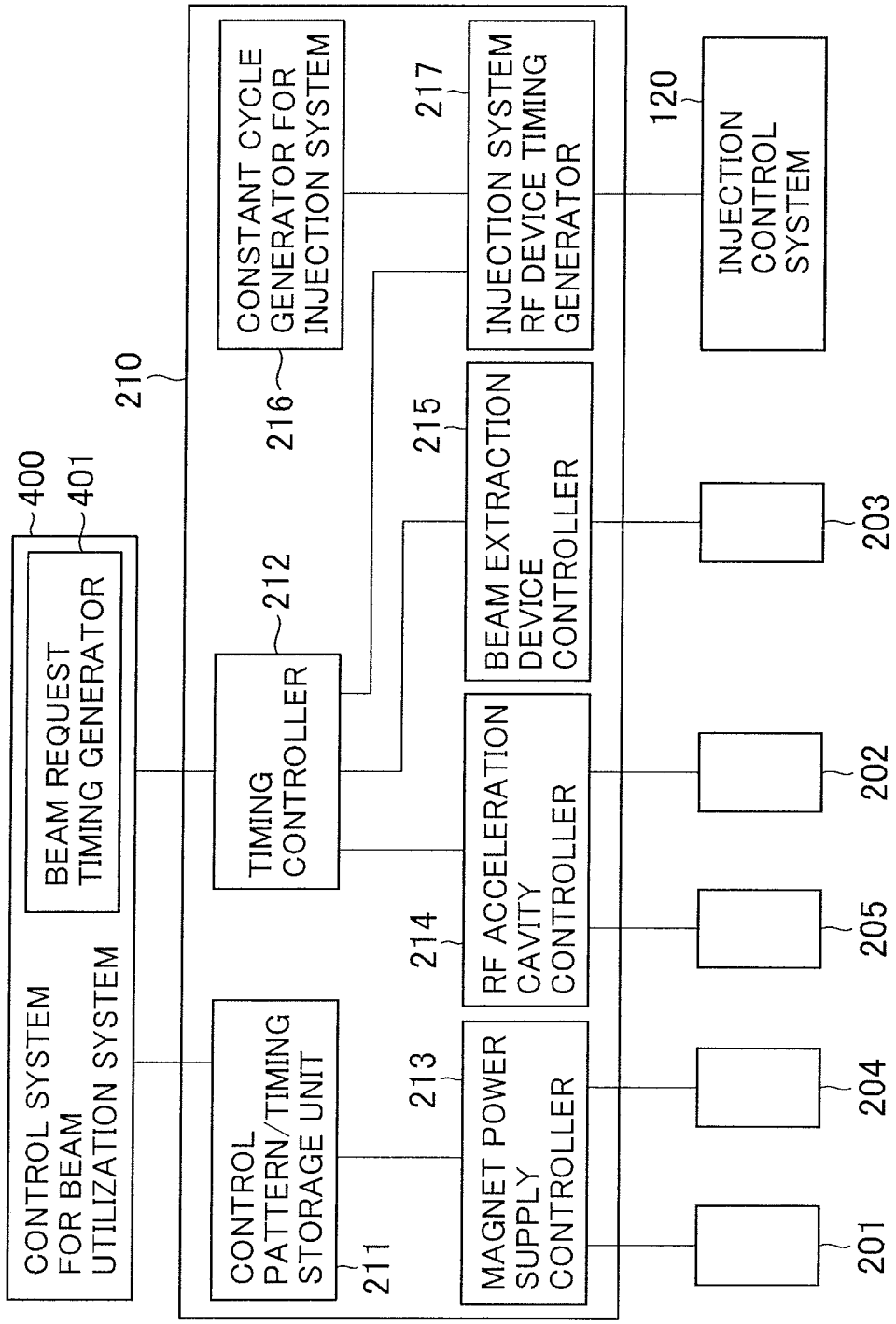
FIG. 4 is a diagram showing in detail an accelerator control device included in the charged particle beam irradiation system according to the first embodiment of the invention.

Details of the accelerator control device 210 that achieves the operation method (shown in FIG. 2) according to the present embodiment are described with reference to FIG. 4. The accelerator control device 210 includes a control pattern/timing storage unit 211. The control pattern/timing storage unit 211 stores the magnet excitation pattern (shown in FIG. 3) of the synchrotron 200 and various control parameters such as an acceleration timing associated with the magnet excitation pattern, an extraction preparation timing associated with the magnet excitation pattern, a deceleration timing associated with the magnet excitation pattern, the generation timing of the injection pretrigger signal. The control pattern/timing storage unit 211 stores the time period $T_{pre}$ so that the time period $T_{pre}$ is associated with the injection timing of the operation cycle of the synchrotron 200 and that the generation timing of the injection pretrigger signal is the time earlier by the time period $T_{pre}$ than the injection timing of the operation cycle of the synchrotron 200. The control pattern/timing storage unit 211 is connected to a magnet power supply controller 213 and controls the bending magnet 201, the beam injection device 204 and the beam extraction device 205, which are included in the synchrotron 200. The timings that are stored in the control pattern/timing storage unit 211 are used to control other devices through a timing controller 212. Specifically, the timing controller 212 controls the RF acceleration cavity 202 through an RF acceleration cavity controller 214 and controls the beam extraction device 203 through a beam extraction device controller 215. The timing controller 212 receives the extraction request signal, the next pattern transition signal or the energy switch request signal from a beam request timing generator 401 that is included in the beam utilization system control device 400. When the timing controller 212 receives the extraction request signal, the timing controller 212 controls the beam extraction device 203 through the beam extraction device controller 215 so that the beam extraction device 203 causes the beam to be extracted from the synchrotron 200.

The basic cycle (constant cycle) $T_{cyc}$ of the radio frequency device operation of the linear accelerator 111 is generated by a beam injection device-dedicated constant cycle generator 216. A beam injection device-dedicated radio frequency device timing generator 217 generates a radio frequency device operation timing of the linear accelerator 111. The beam injection device-dedicated radio frequency device timing generator 217 adjusts the constant basic cycle generated by the beam injection device-dedicated constant cycle generator 216 in accordance with the injection pretrigger signal generated by the timing controller 212 and supplies, as a radio frequency device operation timing, the adjusted cycle to the injection control system 120.

The injection control system 120 repeatedly activates the RF power supply 112 (shown in FIG. 1) and the power supply 102 for the ion source (shown in FIG. 1) while synchronizing the RF power supply 112 and the power supply 102 for the ion source with the radio frequency device operation timing as indicated by the symbol (c) shown in FIG. 2. It is not necessary to accelerate the beam in all cycles of the radio frequency operation. Thus, for example, the beam is set by the method described in Non-Patent Document 3 so as not to be accelerated and is accelerated only at the injection timings as indicated by the symbol (d) shown in FIG. 2. Specifically, the radio frequency operation of the linear accelerator 111 is performed at the timings indicated by the symbol (c) shown in FIG. 2. Among the timings indicated by the symbol (c) shown in FIG. 2, at a timing that does not match any of the injection timings indicated by the symbol (d) shown in FIG. 2, the charged particles that are generated by the ion source 101 are not accelerated, and the linear accelerator 111 operates while not accelerating the charged particles. At a timing that matches any of the injection timing indicated by the symbol (d) shown in FIG. 2, the charged particles that are generated by the ion source 101 are accelerated and injected into the synchrotron 200.

In the above description, the beam injection device-dedicated constant cycle generator 216 and the beam injection device-dedicated radio frequency device timing generator 217 form a part of the accelerator control device 210. However, at least one of the beam injection device-dedicated constant cycle generator 216 and the beam injection device-dedicated radio frequency device timing generator 217 may form a part of the accelerator control device 210. In this case, the aforementioned operations can be achieved.

Figure 5:
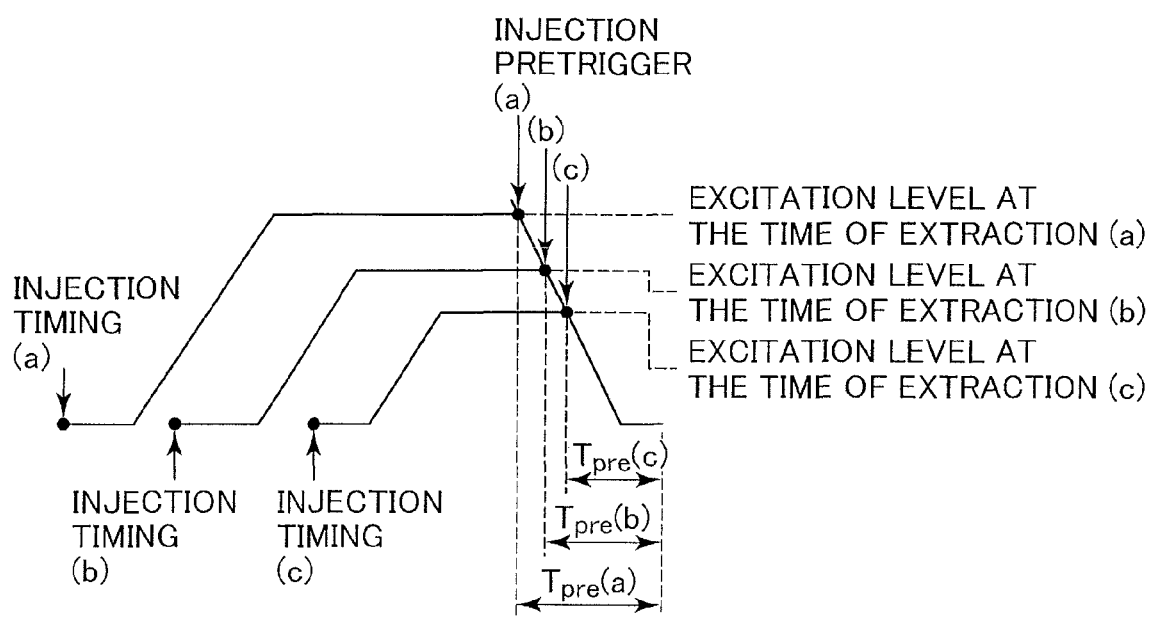
FIG. 5 is a diagram showing differences among operations at excitation levels when a beam is extracted in the operational pattern of the synchrotron included in the charged particle beam irradiation system according to the first embodiment of the invention.

In FIG. 2, as an example of the operations according to the present embodiment, the operation cycle $T_{cyc}$ of the linear accelerator 111 is equal to the time period $T_{pre}$ that ranges from the generation time of the injection pretrigger signal to the injection time of the beam into the synchrotron 200, or $T_{cyc}=T_{pre}$. However, an allowable set range of the time period $T_{pre}$ may vary due to a process of controlling the energy of the beam to be accelerated in the synchrotron 200 and extracted from the synchrotron 200. Thus, the time period $T_{pre}$ may not be equal to the operation cycle $T_{cyc}$ of the linear accelerator 111. For example, the energy of the beam at the time of the extraction may vary as shown in FIG. 5. Specifically, an excitation level of the magnet excitation pattern may vary as indicated by levels (a), (b) and (c) shown in FIG. 5. In addition, when a change rate of current during the deceleration process is set to be constant, the time period for the deceleration process may vary depending on the energy of the beam. Thus, the generation timing of the injection pretrigger signal may vary as indicated by injection pretriggers (a), (b) and (c). Therefore, the time period $T_{pre}$ that ranges from the generation time of the injection pretrigger signal to the injection time of the beam may vary as indicated by time periods $T_{pre}$ (a), $T_{pre}$(b) and $T_{pre}$ (c). In addition, since the capacity of the RF power supply varies depending on the nuclides (for example, proton, carbon) of the particles to be accelerated in the operation cycle $T_{cyc}$ of the linear accelerator 111 and the energy of the accelerated beam, the operation cycle $T_{cyc}$ and the time period $T_{pre}$ are not equal to each other in some cases. Thus, it is necessary to consider the case in which the operation cycle $T_{cyc}$ and the time period $T_{pre}$ are not equal to each other.

Regarding the relationship between the operation cycle $T_{cyc}$ of the linear accelerator 111 and the time period $T_{pre}$ ranging from the generation time of the injection pretrigger signal to the injection time of the beam, when $T_{cyc} < T_{pre}$, it is preferable that the timings be generated so that $T_{cyc} = T_{pre}$ or $T_{cyc} \times N$ (N is an integer)$= T_{pre}$ (FIGS. 2 and 6). Thus, when an operational pattern of the synchrotron is created, and the time period $T_{pre}$ is to be set as a pattern timing, the time period $T_{pre}$ is set so as to satisfy the aforementioned equation. In this case, a new radio frequency of the beam injection device is generated when the operation cycle $T_{cyc}$ elapses after the generation of the injection pretrigger signal. After that, the constant operation cycle $T_{cyc}$ starts. In this manner, the injection timing of the synchrotron 200 can match the time when the linear accelerator 111 can supply the beam.

Regarding the relationship between the operation cycle $T_{cyc}$ of the linear accelerator 111 and the time period $T_{pre}$ ranging from the generation time of the injection pretrigger signal to the injection time of the beam, when $T_{cyc} < T_{pre}$, and the operation cycle $T_{cyc}$ and the time period $T_{pre}$ cannot be set so that $T_{cyc} = T_{pre}$ or $T_{cyc} \times N = T_{pre}$ (N is an integer), a time period $T_{res}$ that satisfies an equation of $T_{pre} = T_{cyc} \times M + T_{res}$ (M is an integer) is calculated. In other words, the time period $T_{res}$ that is the remainder of the division of the time period $T_{pre}$ by an integral multiple of the operation cycle $T_{cyc}$ is calculated. When the sum of the time period $T_{res}$ and a time that elapses from the radio frequency operation timing immediately before the generation of the injection pretrigger signal is larger than the operation cycle $T_{cyc}$, the radio frequency operation timing is generated when the time period $T_{res}$ elapses after the generation of the injection pretrigger signal (refer to FIG. 7). When the sum of the time period $T_{res}$ and the time that elapses from the radio frequency operation timing immediately before the generation of the injection pretrigger signal is smaller than the operation cycle $T_{cyc}$, the radio frequency operation timing is generated when a time period of $T_{res} + T_{cyc}$ elapses after the generation of the injection pretrigger signal (refer to FIG. 8). In each of the cases, a new radio frequency of the beam injection device is generated. After that, the constant operation cycle $T_{cyc}$ starts. In this manner, the injection timing of the synchrotron 200 can match the time when the linear accelerator 111 can supply the beam.

Figure 10:
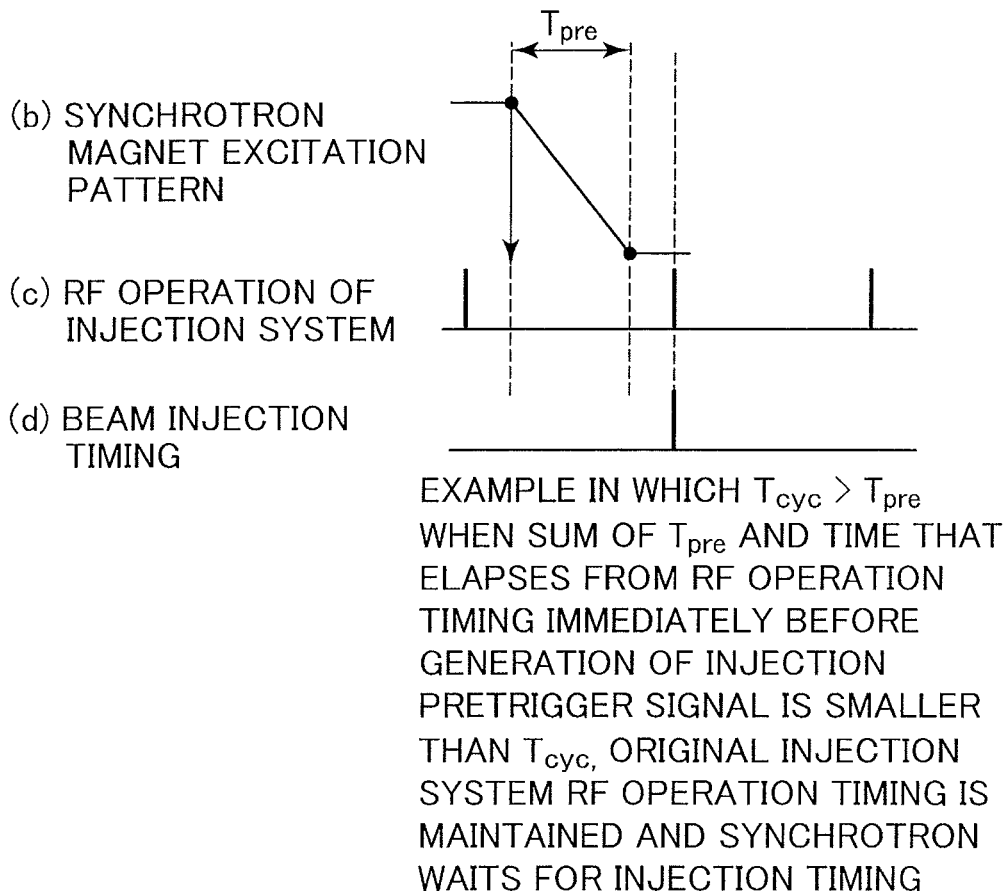
FIG. 10 is a timing chart of another example of the operations of the charged particle beam irradiation system according to the first embodiment of the invention.

Regarding the relationship between the operation cycle $T_{cyc}$ of the linear accelerator 111 and the time period $T_{pre}$ ranging from the generation time of the injection pretrigger signal to the injection time of the beam, when $T_{cyc} > T_{pre}$, and the sum of the time period $T_{pre}$ and the time that elapses from the radio frequency operation timing immediately before the generation of the injection pretrigger signal is larger than the operation cycle $T_{cyc}$, the radio frequency operation timing is generated when the time period $T_{pre}$ elapses after the generation of the injection pretrigger signal (refer to FIG. 9). When the sum of the time period $T_{pre}$ and the time that elapses from the radio frequency operation timing immediately before the generation of the injection pretrigger signal is smaller than the operation cycle $T_{cyc}$, the original timing of the radio frequency operation of the beam injection device is maintained and the synchrotron 200 waits for the injection timing (refer to FIG. 10). In operations shown in FIG. 10, although the effects of the present invention are not obtained, a waiting time can be reduced by combining the operations shown in FIG. 10 with the operations shown in FIG. 9. However, since the effects are small, it is preferable that the timings be set so that the operation cycle $T_{cyc}$ of the linear accelerator 200 is shorter than the time period $T_{pre}$ that ranges from the generation time of the injection pretrigger signal to the injection time of the beam to prevent the operations shown in FIGS. 9 and 10. The optimal relationship between the operation cycle $T_{cyc}$ and the time period $T_{pre}$ is the relationship of $T_{cyc} = T_{pre}$ or the relationship of $T_{cyc} \times N = T_{pre}$ (N is an integer) as shown in FIG. 6. When the operation cycle $T_{cyc}$ and the time period $T_{pre}$ cannot be set so that $T_{cyc} = T_{pre}$ or $T_{cyc} \times N = T_{pre}$ the optimal relationship is the relationship of $T_{cyc} < T_{pre}$ as shown in FIG. 7.

Figure 11:
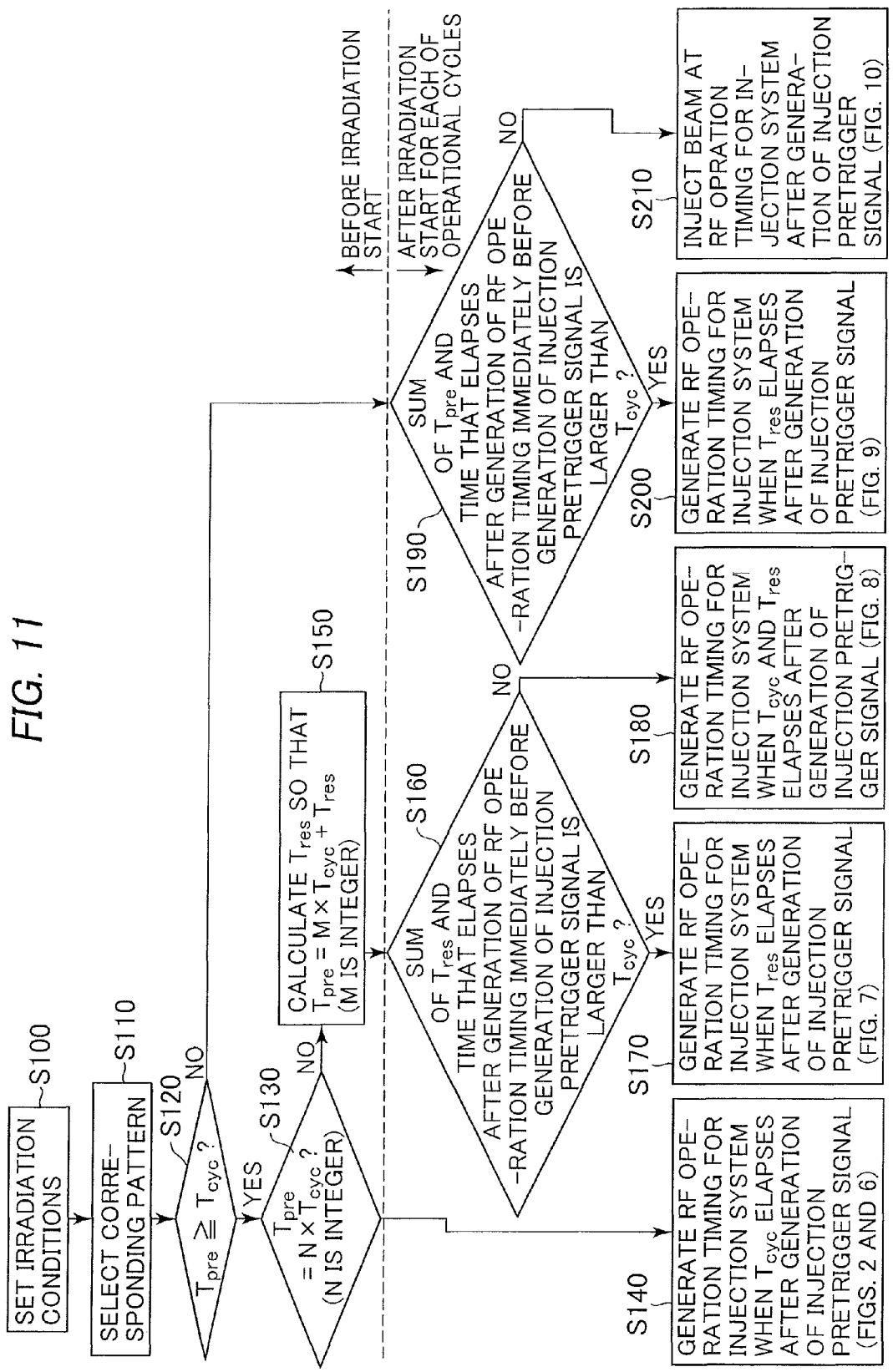
FIG. 11 is a flowchart of a process of determining an operation of the charged particle beam irradiation system according to the first embodiment of the invention.

FIG. 11 is a flowchart of a process of determining a relationship between the operation cycle $T_{cyc}$ of the linear accelerator 111 and the time period $T_{pre}$ ranging from the generation time of the injection pretrigger signal to the injection time of the beam, the relationships being shown in FIGS. 2, 6 to 10. The process of determining the relationship is described with reference to FIG. 4 showing the configuration of the control device 210. Conditions for irradiation with the charged particle beam to be utilized by the beam utilization system 500 are set by the beam utilization system control device 400 (in step S100). A corresponding pattern is selected from the data stored in the control pattern/timing storage unit 211 included in the accelerator control device 210 (in step S110). The operation cycle $T_{cyc}$ is known as a characteristic value of the linear accelerator 111. Thus, the timing controller 212 can detect the relationship between $T_{cyc}$ and $T_{pre}$. The timing controller 212 determines whether or not the time period $T_{pre}$ is equal to or larger than the operation cycle $T_{cyc}$ (in step S120). When $T_{pre} \geq T_{cyc}$, the timing controller 212 determines whether or not $T_{cyc} \times N = T_{pre}$ (N is an integer) (in step S130). When $T_{pre} \geq T_{cyc}$, and $T_{cyc} \times N = T_{pre}$ (N is an integer), irradiation with the beam starts. The beam injection device-dedicated radio frequency device timing generator 217 generates the radio frequency operation timing of the linear accelerator 111 when the operation cycle $T_{cyc}$ elapses after the generation of the injection pretrigger signal, and the beam injection device-dedicated radio frequency device timing generator 217 causes the beam injection device radio frequency device to operate (in step S140).

When a value of $T_{cyc} \times N$ (N is an integer) is not equal to $T_{pre}$ in step S130, the timing controller 212 calculates a time period $T_{res}$ so that $T_{pre} = T_{cyc} \times M + T_{res}$ (M is an integer) (in step S150). Then, the irradiation with the beam starts. After the irradiation starts, the timing controller 212 generates an injection pretrigger signal timing on the basis of an operational pattern (of the synchrotron 200) that is specified on the basis of the extraction request signal, the next pattern transition signal or the energy switch request signal, which is transmitted from the beam utilization system 400. The beam injection device-dedicated radio frequency device timing generator 217 determines, on the basis of the relationship between the generation time of the injection pretrigger signal and the basic cycle (constant cycle) generated by the beam injection device-dedicated constant cycle generator 216, whether or not the sum of the time period $T_{res}$ and the time that elapses after the radio frequency operation timing immediately before the generation of the injection pretrigger signal is larger than the operation cycle $T_{cyc}$ for each of operation cycles of the synchrotron 200 (in step S160). The beam injection device-dedicated radio frequency device timing generator 217 generates the radio frequency operation timing of the linear accelerator 111 on the basis of the result of the determination and causes the beam injection device radio frequency device to operate (in step S170 or S180).

When the timing controller 212 determines that the time period $T_{pre}$ is smaller than the operation cycle $T_{cyc}$ (in step S120), the irradiation with the beam starts. After the irradiation starts, the timing controller 212 generates the injection pretrigger signal timing in a similar manner to the case in which $T_{cyc} \times N = T_{pre}$ (N is an integer), and the beam injection device-dedicated radio frequency device timing generator 217 determines whether or not the sum of the time period $T_{res}$ and the time that elapses after the radio frequency operation timing immediately before the generation of the injection pretrigger signal is larger than the operation cycle $T_{cyc}$ (in step S190). The beam injection device-dedicated radio frequency device timing generator 217 generates the radio frequency operation timing of the linear accelerator 111 on the basis of the result of the determination and causes the beam injection device radio frequency device to operate (in step S200 or S210).

The determination method is not limited to the aforementioned method. Another determination method may be performed as long as the relationships among the magnet excitation pattern (b) of the synchrotron, the radio frequency operation (c) of the beam injection device and the beam injection timing (d), which are shown in any of FIGS. 6 to 10, are established.

Examples of the effects of the present embodiment are described using detailed values. It is assumed that the radio frequency operation cycle $T_{cyc}$ of the beam injection device is set to 0.5 seconds, the operation cycle of the synchrotron 200 is set to 2.2 seconds, the injection pretrigger signal is set so that the $T_{pre} = T_{cyc}$, and the synchrotron 200 operates for 20 constant operation cycles. In this assumption, when the present invention is not applied, it takes a waiting time of 0.3 seconds for the operation cycle of the synchrotron and the operation cycle of the beam injection device to be matched after the synchrotron operates for the cycle of 2.2 seconds. Thus, the actual operation cycle of the synchrotron becomes 2.5 seconds, and the operational time of the synchrotron is 2.5 seconds×20=50 seconds. In the aforementioned assumption, when the present invention is applied, the actual operation cycle of the synchrotron is 2.2 seconds, and the operational time of the synchrotron is 2.2 seconds×20=44 seconds. The operational time can be reduced by 12%.

In the present embodiment as described above, the pretrigger timing (injection pretrigger signal) that is used to notify the linear accelerator 111 of the requested injection timing after the completion of the extraction process is set for timing control that is used to control the injection process, the acceleration process, the extraction process and the deceleration process in the synchrotron 200. After the completion of the process of causing the charged particle beam to be extracted from the synchrotron 200, the operation timing of the linear accelerator 111 is changed so that the operation cycle of the linear accelerator 111 temporarily increases. Thus, the charged particle beam can be injected into the synchrotron 200 at an arbitrary timing while a lower limit of the operation cycle of the linear accelerator 111 is maintained. The synchrotron 200 can receives the charged particle beam injected from the linear accelerator 111 at the injection timing requested by the synchrotron 200.

In the present embodiment, since the synchrotron 200 can receives the charged particle beam injected from the linear accelerator 111 at the injection timing requested by the synchrotron 200, it is possible to reduce the time for irradiation of a tumor and thereby reduce the time for therapy, and the system can efficiently operate in the irradiation device utilizing the charged particle beam accelerated by the synchrotron 200.

Second Embodiment

Figure 12:
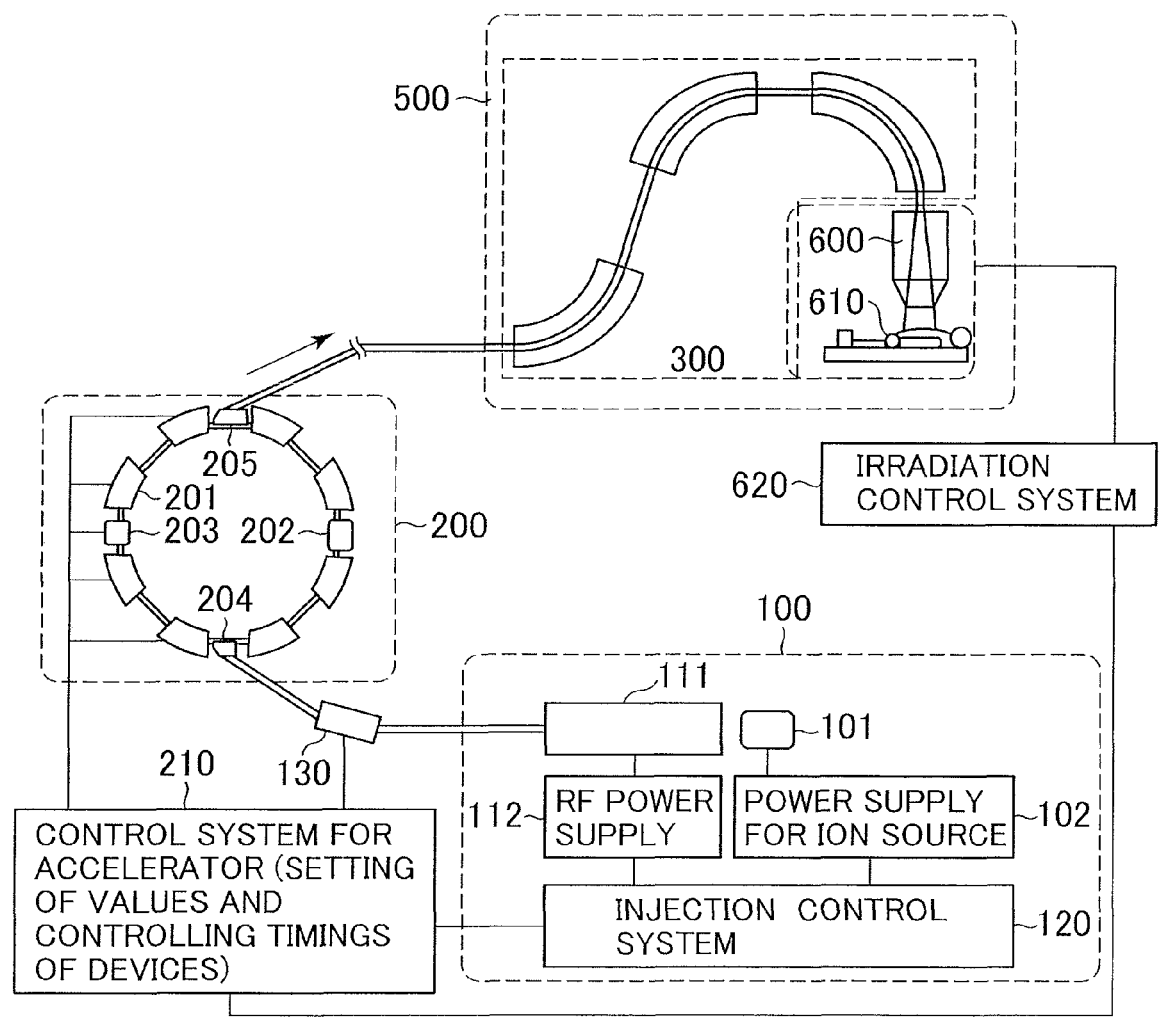
FIG. 12 is an outline diagram showing the entire configuration of a charged particle beam irradiation system according to a second embodiment of the invention.

Next, a charged particle beam irradiation system according to a second embodiment of the present invention is described with reference to FIGS. 12 to 14. The charged particle beam irradiation system according to the second embodiment includes an irradiation device 600 that irradiates a tumor (such as cancer) of a patient with a charged particle beam (ion beam) such as protons or carbon ions, and thereby performs a therapy. The irradiation device 600 is provided as the beam utilization system 500 according to the first embodiment.

In the second embodiment, the charged particle beam is transported from the synchrotron 200 through the beam transport system 300 to the irradiation device 600. The irradiation device 600 is described with reference to FIG. 13. The irradiation device 600 has an X-direction scanning magnet 601A and a Y-direction scanning magnet 601B that scan a tumor 611 of a patient 610 with the charged particle beam (guided by the beam transport system 300) in a horizontal direction (X direction shown in FIG. 13) and a vertical direction (direction (Y direction) perpendicular to the sheet of FIG. 13). The charged particle beam that is deflected by the X-direction scanning magnet 601A and the Y-direction scanning magnet 601B passes through a beam position monitor 602 and a dose monitor 603 so that the tumor 611 is irradiated with the charged particle beam. The beam position monitor 602 measures the position and width (spreading) of the charged particle beam. The dose monitor 603 measures an irradiation dose of the charged particle beam.

The irradiation using a beam scanning method is described with reference to FIGS. 13 and 14. FIG. 14 is a diagram showing the tumor 611 when viewed from the upstream side of the charged particle beam.

Figure 13:
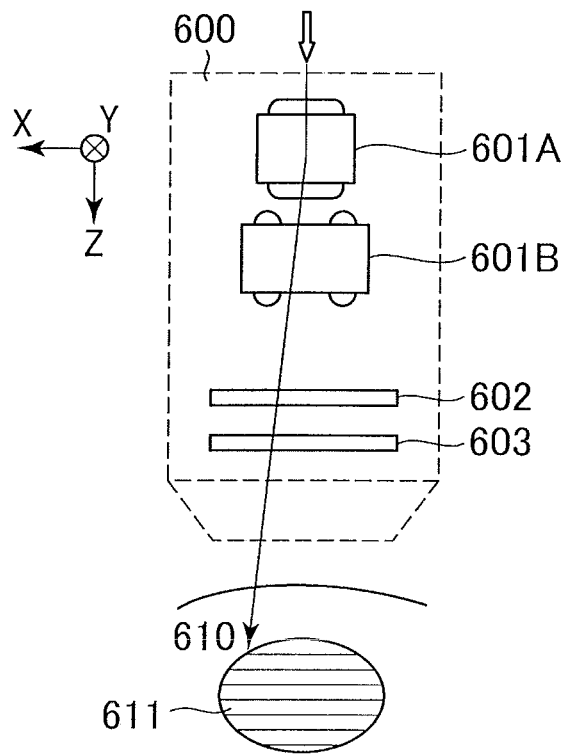
FIG. 13 is a diagram showing the configuration of an irradiation device included in the charged particle beam irradiation system according to the second embodiment of the invention.

As shown in FIG. 13, the tumor 611 of the patient 610 is three-dimensionally divided into a plurality of layers in a depth direction (Z direction in FIG. 13). The layers are each two-dimensionally divided into a plurality of spots 612 (hereinafter referred to as irradiation spots). The depth direction corresponds to a depth that the charged particle beam reaches. The depth that the charged particle beam reaches is changed by changing the energy of the charged particle beam to be extracted from the synchrotron 200 so that the layers can be selectively irradiated. The scanning magnets 601A and 601B deflects the charged particle beam so as to two-dimensionally scan each of the layers with the charged particle beam along an irradiation path 613 so that a predetermined dose is provided to each of the irradiation spots as shown in FIG. 14, for example. The dose of the charged particle beam with which each of the irradiation spots is irradiated is measured by the dose monitor 603. The position and spreading of the charged particle beam are measured by the beam position monitor 602.

In the irradiation method according to the present embodiment, when charged particles that are stored in the synchrotron 200 are depleted during the irradiation of the irradiation spots (shown in FIG. 14) included in any of the layers or when a time period for irradiation that can be performed for one operation cycle of the synchrotron 200 is not sufficient and elapses during the irradiation of the irradiation spots (shown in FIG. 14) included in the layer, a request for a transition to the next pattern is provided to the synchrotron 200. In each of the cases, the extraction of the beam from the synchrotron 200 during the operation cycle may be stopped, and the timing of the transition to the next pattern may not be constant.

Figure 14:
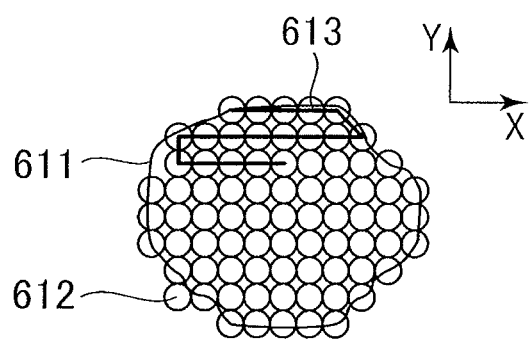
FIG. 14 is a diagram showing spots set in a specific layer that is included in a tumor to be irradiated by the charged particle beam irradiation system according to the second embodiment of the invention and is divided in a depth direction, the diagram further showing a beam scanning path.

When the irradiation of all the irradiation spots of the layer shown in FIG. 14 is completed, the depth that the charged particle beam reaches in the depth direction (Z direction) needs to be changed. Thus, the energy of the beam extracted from the synchrotron 200 is changed. In this case, since a time period for the irradiation of each of the layers varies depending on the shape of the tumor 611, the timing of completion of the extraction in the operation cycle of the synchrotron 200 may not be constant.

As described above, the operation cycle of the synchrotron 200 and the timing of the extraction from the synchrotron 200 are not constant when the irradiation device 600 is used in the present embodiment. Thus, when the cycle of the radio frequency operation of the linear accelerator 111 is fixed, the charged particle beam may not be injected into the synchrotron 200 at an injection timing desired for the synchrotron 200, and the irradiation time period may be increased.

In the present embodiment, when the charged particles that are stored in the synchrotron 200 are depleted during the irradiation of the irradiation spots (shown in FIG. 14) included in any of the layers, or when the time period for irradiation that can be performed during one cycle of the synchrotron 200 is not sufficient and elapses during the irradiation of the irradiation spots (shown in FIG. 14) included in the layer, the accelerator control device 210 (first control device) generates and outputs the next pattern transition request signal that indicates a request for a transition of the operational pattern of the synchrotron 200. In addition, when the irradiation of all the spots (shown in FIG. 14) of any of the layers is completed, the irradiation control device 620 (first control device) outputs the energy switch request signal that indicates a request for a change in the energy of the beam extracted from the synchrotron 200. The accelerator control device 210 (control device, second control device) performs the operation method (shown in FIG. 2) according to the present invention when the accelerator control device 210 generates the next pattern transition request signal or when the accelerator control device 210 receives the energy switch request signal, and changes the operation timing of the linear accelerator 111 on the basis of the pretrigger timing (injection pretrigger signal) so that the operation cycle of the linear accelerator 111 temporarily increases. Thus, the injection timing can be set to a desired timing. Therefore, the irradiation time period is not increased, the time for the therapy can be reduced. Thus, the system can efficiently operate.

Examples of the effects of the present embodiment are described using detailed values. It is assumed that a target to be irradiated is a cube that has sides of 10 cm and a volume of 1 litter; the number of irradiation spots that are necessary to irradiate the cube is 10,000; the number of layers (of the target) divided in the depth direction (Z direction) is 30; and it is necessary that the total of the number of changes of the operation cycle of the synchrotron 200 and the number of changes of the energy be 40 during irradiation. The reason that the number of the divided layers does not match the total of the number of changes of the operation cycle of the synchrotron 200 and the number of changes of the energy is that when the amount of charged particles with which each of the layers is irradiated is large, the amount of charged particles that can be extracted for one operation cycle of the synchrotron 200 is not sufficient and each of the layers is irradiated for a plurality of operation cycles of the synchrotron 200. In this assumption, when the radio frequency operation cycle $T_{cyc}$ of the beam injection device is set to 0.5 seconds and the present invention is applied, a waiting time does not occur immediately before the cycle. In the assumption, when the radio frequency operation cycle $T_{cyc}$ of the beam injection device is set to 0.5 seconds and the present invention is not applied, a waiting time of up to 0.5 seconds occurs immediately before the cycle. However, the waiting time may not occur by accident. When a waiting time of 0.25 seconds, which is an intermediate value, is set to occur immediately before each radio frequency operation cycle of the beam injection device, and the operation cycle is changed 40 times, the irradiation time is increased by 10 seconds. When the irradiation time in the case where the present invention is not applied is set to, for example, approximately 100 seconds, the irradiation time is reduced by 10 seconds that correspond to a 10% reduction.

Third Embodiment

Figure 15:
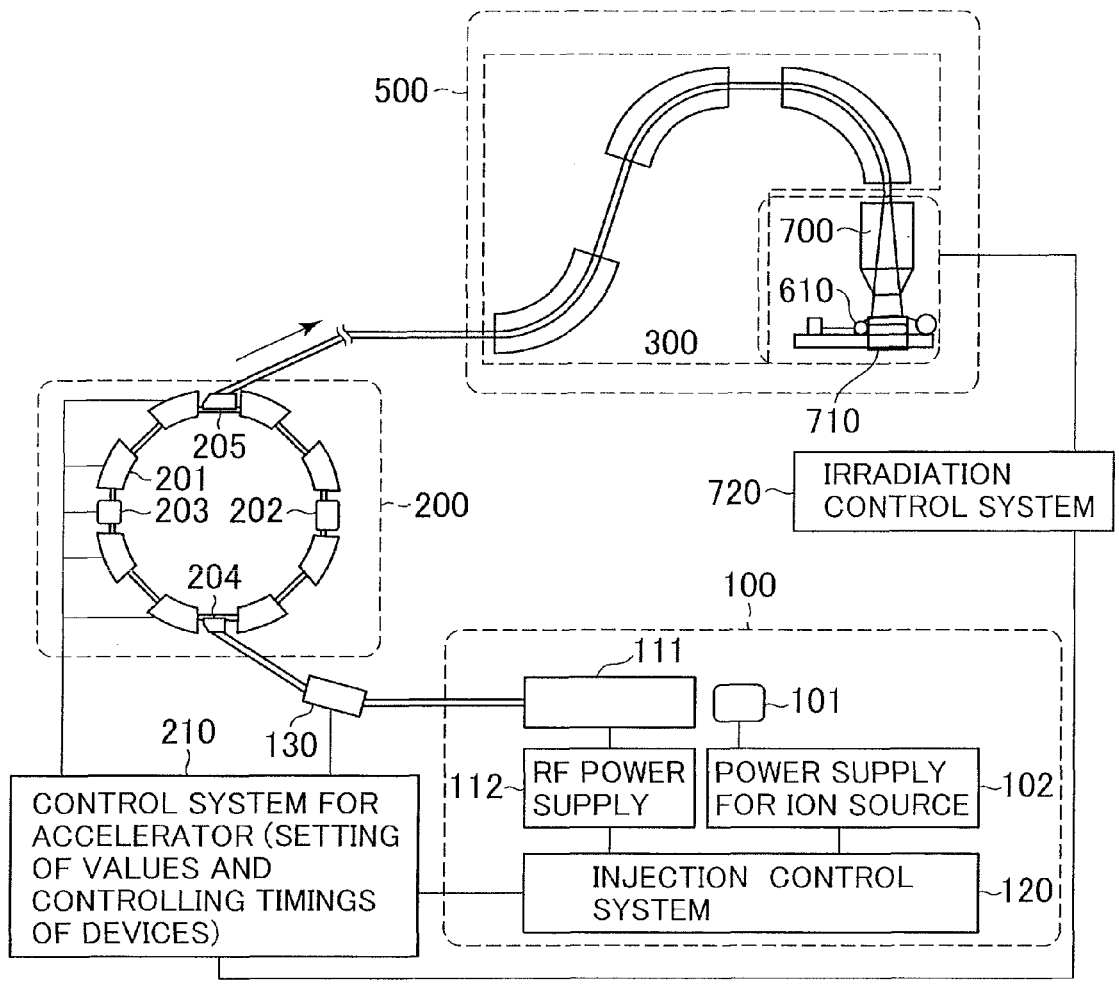
FIG. 15 is an outline diagram showing the entire configuration of a charged particle beam irradiation system according to a third embodiment of the invention.

Next, a charged particle beam irradiation system according to a third embodiment of the present invention is described with reference to FIGS. 15 and 16. The charged particle beam irradiation system according to the third embodiment includes an irradiation device 700 that irradiates a tumor (such as cancer) of a patient with a charged particle beam (ion beam) such as protons or carbon ions, and thereby performs a therapy. The irradiation device 700 is provided as the beam utilization system 500 according to the first embodiment. In addition, the irradiation system includes a unit that detects a movement (caused by breathing of the patient) of the tumor and movements of others.

In the present embodiment, charged particles are transported from the synchrotron 200 through the beam transport system 300 to the irradiation device 700. The irradiation device 700 is described with reference to FIG. 13. A method for forming an irradiation field by the irradiation device 700 may be any method for forming an irradiation field, such as a scatterer method using scattering of a charged particle beam or the aforementioned scanning method. A detecting unit 710 is provided to detect a movement of the tumor 611 of the patient 610. In order to achieve an irradiation of the tumor with high accuracy, a method for detecting a movement of the tumor and irradiating the tumor only when the movement is in a predetermined range has been proposed. As a method that is performed by the detecting unit 710, a method for monitoring a movement of a body surface to detect a respiratory movement, a method for monitoring respiratory air flow caused by respiration and inspired air flow in the vicinity of the mouth of the patient, and a method for directly monitoring the position of the tumor or a marker of the tumor using an X ray transparent image or the like may be used.

Figure 16:
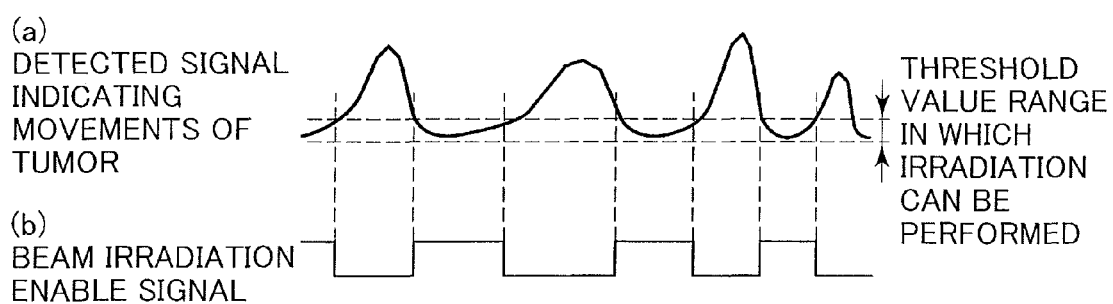
FIGS. 16(a) and 16(b) are diagrams showing the relationship between a tumor movement detection signal and a beam irradiation enable signal that are generated by the charged particle beam irradiation system according to the third embodiment of the invention.

FIGS. 16(a) and 16(b) are diagrams showing the relationship between detection of a movement of the tumor and irradiation with the beam. FIG. 16(a) shows a detected signal indicating movements of the tumor and a threshold range of the signal. When a value of the signal is in the threshold range, the tumor is located at a desired position or located in a desired range including the desired position. Only when the value of the detected signal (tumor position detection signal) is in the threshold range, the tumor is irradiated with the beam. In this case, times when the irradiation device 700 according to the present embodiment can irradiate the tumor are shown in FIG. 16(*b*). Since the signal indicates the movements of the patient, the times may not be constant.

As described above, when the irradiation device 700 according to the present embodiment is used, the operation cycle of the synchrotron 200 and the timing of the extraction are not constant. When the cycle of the radio frequency operation of the linear accelerator 111 is fixed, the charged particle beam cannot, be injected into the synchrotron 200 at the injection timing desired for the synchrotron 200. Thus, the irradiation time period may be increased.

In the present embodiment, the irradiation control device 720 sets a timing of a time period for which the target to be irradiated can be irradiated on the basis of the signal obtained by the detection of the movements of the target to be irradiated as shown in FIG. 16(*b*). In addition, the irradiation control device 720 (first control device) outputs a beam extraction request signal to request the extraction of the beam only for the time period for which the target to be irradiated can be irradiated on the basis of the signal. The accelerator control device 210 (control device, second control device) receives the signal, performs the operation method (shown in FIG. 2) according to the present invention and changes the operation timing of the linear accelerator 111 on the basis of the pretrigger timing (injection pretrigger signal) so that the operation cycle of the linear accelerator 111 temporarily increases. Thus, the injection timing can be set to a desired timing. Therefore, the irradiation time period is not increased, the time for the therapy can be reduced, and the system can efficiently operate.

What is claimed is:

1. A method for operating a charged particle beam generator that includes a linear accelerator and a circular accelerator,
wherein the linear accelerator operates in a predetermined operation cycle on the basis of a radiofrequency power supply for applying a pulse voltage for acceleration, and accelerates, at an operation timing based on the operation cycle, charged particles extracted from an ion source so as to cause a charged particle beam to be extracted from the linear accelerator; and
wherein the circular accelerator operates in an operation cycle including a process of causing the charged particle beam to be injected into the circular accelerator, a process of accelerating the charged particle beam, a process of causing the charged particle beam to be extracted from the circular accelerator and a process of decelerating the charged particle beam, causes the charged particle beam accelerated by the linear accelerator to be injected into the circular accelerator at a predetermined timing, and causes the accelerated charged particle beam to be extracted from the circular accelerator,
the method comprising the step of changing the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches an injection timing of the next operation cycle of the circular accelerator.

2. The method according to claim 1,
wherein after the completion of the process of causing the charged particle beam to be extracted from the circular accelerator in the operation cycle of the circular accelerator, a timing signal that notifies the linear accelerator of the injection timing of the next operation cycle of the circular accelerator is generated, and the operation timing of the linear accelerator is changed on the basis of the timing signal so that the operation cycle of the linear accelerator temporarily increases.

3. The method according to claim 2,
wherein the timing signal is set so that a time period that ranges from the time of the generation of the timing signal to the injection timing of the next operation cycle of the circular accelerator is equal to an integral multiple of the operation cycle of the linear accelerator, and
wherein the operation timing of the linear accelerator is generated when one operation cycle of the linear accelerator elapses after the generation of the timing signal.

4. The method according to claim 2,
wherein the timing signal is set so that a time period that ranges from the time of the generation of the timing signal to the injection timing of the next operation cycle of the circular accelerator is equal to the sum of an integral multiple of the operation cycle of the linear accelerator and a certain time period that is shorter than the operation cycle of the linear accelerator,
wherein when the operation timing of the linear accelerator is immediately before the generation of the timing signal, and the sum of the certain time period and a time period that ranges from the operation timing of the linear accelerator to the time of the generation of the timing signal is larger than one operation cycle of the linear accelerator, the operation timing of the linear accelerator is generated when the certain time period elapses after the generation of the timing signal, and
wherein when the operation timing of the linear accelerator is immediately before the generation of the timing signal, and the sum of the certain time period and a time period that ranges from the operation timing of the linear accelerator to the time of the generation of the timing signal is not larger than one operation cycle of the linear accelerator, the operation timing of the linear accelerator is generated when the sum of the certain time period and one operation cycle of the linear accelerator elapses after the generation of the timing signal.

5. A method for operating a charged particle irradiation system that includes a linear accelerator, a circular accelerator, and an irradiation device,
wherein the linear accelerator operates in a predetermined operation cycle on the basis of a radiofrequency power supply for applying a pulse voltage for acceleration, and accelerates, at an operation timing based on the operation cycle, charged particles extracted from an ion source so as to cause a charged particle beam to be extracted from the linear accelerator,
wherein the circular accelerator operates in an operation cycle including a process of causing the charged particle beam to be injected into the circular accelerator, a process of accelerating the charged particle beam, a process of causing the charged particle beam to be extracted from the circular accelerator and a process of decelerating the charged particle beam, causes the charged particle beam accelerated by the linear accelerator to be injected into the circular accelerator at a predetermined timing, and causes the accelerated charged particle beam to be extracted from the circular accelerator, and
wherein the irradiation device radiates the charged particle beam extracted from the circular accelerator, the method comprising the steps of:

controlling an extractor of the circular accelerator in the process of causing the charged particle beam to be extracted from the circular accelerator in the operation cycle of the circular accelerator so that the charged particle beam is extracted from the circular accelerator only for a time period requested from the irradiation device; and changing the operation timing of the linear accelerator after the process of causing the charged particle beam to be extracted from the circular accelerator in the operation cycle of the circular accelerator is completed by the control of the extractor so that the operation cycle of the linear accelerator temporarily increases and the operation timing of the linear accelerator matches an injection timing of the next operation cycle of the circular accelerator.

6. A method for operating a charged particle irradiation system that includes a linear accelerator, a circular accelerator, and irradiation device, wherein the linear accelerator operates in a predetermined operation cycle on the basis of a radiofrequency power supply for applying a pulse voltage for acceleration, and accelerates, at an operation timing based on the operation cycle, charged particles extracted from an ion source so as to cause a charged particle beam to be extracted from the linear accelerator, wherein the circular accelerator operates in an operation cycle including a process of causing the charged particle beam to be injected into the circular accelerator, a process of accelerating the charged particle beam, a process of causing the charged particle beam to be extracted from the circular accelerator and a process of decelerating the charged particle beam, causes the charged particle beam accelerated by the linear accelerator to be injected into the circular accelerator at a predetermined timing, and causes the accelerated charged particle beam to be extracted from the circular accelerator, and wherein the irradiation device has a scanning magnet for deflecting the charged particle beam extracted from the circular accelerator so as to scan a target with the charged particle beam and irradiates the target with the charged particle beam that has passed through the scanning magnet, the method comprising the steps of:

controlling a excitation current to be applied to the scanning magnet, scanning, with the charged particle beam, one of a plurality of layers into which the target to be irradiated with the charged particle beam is divided in a depth direction; and after completion of the scanning of the one layer with the charged particle beam, outputting an energy switch request indicating a request for a change in the energy of the charged particle beam to be extracted from the circular accelerator in order to scan another one of the layers with the charged particle beam; and changing the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches an injection timing of the next operation cycle of the circular accelerator in order to change the operation cycle of the circular accelerator to the next operation cycle on the basis of the energy switch request.

7. A method for operating a charged particle irradiation system that includes a linear accelerator, a circular accelerator, and an irradiation device, wherein the linear accelerator operates in a predetermined operation cycle on the basis of a radiofrequency power supply for applying a pulse voltage for acceleration, and accelerates, at an operation timing based on the operation cycle, charged particles extracted from an ion source so as to cause a charged particle beam to be extracted from the linear accelerator, wherein the circular accelerator operates in an operation cycle including a process of causing the charged particle beam to be injected into the circular accelerator, a process of accelerating the charged particle beam, a process of causing the charged particle beam to be extracted from the circular accelerator and a process of decelerating the charged particle beam, causes the charged particle beam accelerated by the linear accelerator to be injected into the circular accelerator at a predetermined timing, and causes the accelerated charged particle beam to be extracted from the circular accelerator, and wherein the irradiation device has a scanning magnet for deflecting the charged particle beam extracted from the circular accelerator so as to scan a target with the charged particle beam and irradiates the target with the charged particle beam that has passed through the scanning magnet, the method comprising the steps of:

controlling an excitation current to be applied to the scanning magnet, scanning a target with the charged particle beam, when charged particles that are stored in the circular accelerator are depleted during the scanning with the charged particle beam or when a time for irradiation that can be performed during one cycle of the circular accelerator is not sufficient and elapses during the scanning with the charged particle beam, stopping the process of causing the charged particle beam to be extracted from the circular accelerator in the operation cycle of the circular accelerator, and outputting an operational pattern transition request indicating a request for a transition to an operational pattern of the next operation cycle; and changing the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches an injection timing of the next operation cycle of the circular accelerator in order to change the operation cycle of the circular accelerator to the next operation cycle on the basis of the operational pattern transition request.

8. A method for operating a charged particle irradiation system that includes a linear accelerator, a circular accelerator, and an irradiation device, wherein the linear accelerator operates in a predetermined operation cycle on the basis of a radiofrequency power supply for applying a pulse voltage for acceleration, and accelerates, at an operation timing based on the operation cycle, charged particles extracted from an ion source so as to cause a charged particle beam to be extracted from the linear accelerator, wherein the circular accelerator operates in an operation cycle including a process of causing the charged particle beam to be injected into the circular accelerator, a process of accelerating the charged particle beam, a process of causing the charged particle beam to be extracted from the circular accelerator and a process of decelerating the charged particle beam, causes the charged particle beam accelerated by the linear accelerator to be injected into the circular accelerator at a predetermined timing, and causes the accelerated charged particle beam to be extracted from the circular accelerator, and wherein the irradiation device temporally or spatially forms the charged particle beam extracted from the circular accelerator and irradiates a target with the charged particle beam so that the shape of the target matches a region to be irradiated with the charged particle beam, the method comprising the steps of:

setting, on the basis of a signal obtained by a detection of a movement of the target to be irradiated, a timing of a time period for which the target can be irradiated, and outputting a beam request that indicates a request to extract the charged particle beam only for the time period; and changing the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches an injection timing of the next operation cycle of the circular accelerator in order to change the operation cycle of the circular accelerator to the next operation cycle on the basis of the beam request.

9. A charged particle beam generator comprising:

a linear accelerator that operates in a predetermined operation cycle on the basis of a radiofrequency power supply for applying a pulse voltage for acceleration, and accelerates, at an operation timing based on the operation cycle, charged particles extracted from an ion source so as to cause a charged particle beam to be extracted from the linear accelerator;

a circular accelerator that operates in an operation cycle including a process of causing the charged particle beam to be injected into the circular accelerator, a process of accelerating the charged particle beam, a process of causing the charged particle beam to be extracted from the circular accelerator and a process of decelerating the charged particle beam, causes the charged particle beam accelerated by the linear accelerator to be injected into the circular accelerator at a predetermined timing and causes the accelerated charged particle beam to be extracted from the circular accelerator; and a control device that changes the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches an injection timing of the next operation cycle of the circular accelerator.

10. The charged particle beam generator according to claim 9, wherein the control device generates a timing signal notifying the linear accelerator of the injection timing of the next operation cycle of the circular accelerator after completion of the process of causing the charged particle beam to be extracted from the circular accelerator in the operation cycle of the circular accelerator, and changes the operation timing of the linear accelerator so that the operation cycle of the linear accelerator temporarily increases.

11. The charged particle beam generator according to claim 10, wherein the control device sets the timing signal so that a time period that ranges from the time of the generation of the timing signal to the injection timing of the next operation cycle of the circular accelerator is equal to an integral multiple of the operation cycle of the linear accelerator, and wherein the control device generates the operation timing of the linear accelerator when one operation cycle of the linear accelerator elapses after the generation of the timing signal.

12. The charged particle beam generator according to claim 10, wherein the control device sets the timing signal so that a time period that ranges from the time of the generation of the timing signal to the injection timing of the next operation cycle of the circular accelerator is equal to the sum of an integral multiple of the operation cycle of the linear accelerator and a certain time period that is shorter than the operation cycle of the linear accelerator, wherein when the operation timing of the linear accelerator is immediately before the generation of the timing signal, and the sum of the certain time period and a time period ranging from the operation timing of the linear accelerator to the time of the generation of the timing signal is larger than one operation cycle of the linear accelerator, the control device generates the operation timing of the linear accelerator when the certain time period elapses after the generation of the timing signal, and wherein the operation timing of the linear accelerator is immediately before the generation of the timing signal, and the sum of the certain time period and a time period ranging from the operation timing of the linear accelerator to the time of the generation of the timing signal is not larger than one operation cycle of the linear accelerator, the control device sets the operation timing of the linear accelerator to the time when the sum of one operation cycle of the linear accelerator and the certain time period elapses after the generation of the timing signal.

13. The charged particle beam generator according to claim 9, wherein the control device includes:

a storage device that stores an injection pretrigger signal timing notifying the linear accelerator of the injection timing of the next operation cycle of the circular accelerator and timings related to an operational pattern including the process of causing the charged particle beam to be injected into the circular accelerator, the process of accelerating the charged particle beam, the process of causing the charged particle beam to be extracted from the circular accelerator and the process of decelerating the charged particle beam;

a timing control device that receives a request to update the operational pattern and receives information on the timings stored in the storage device;

a constant cycle generator that generates a basic operation cycle of the linear accelerator; and a radiofrequency device timing generator that adjusts the basic operation cycle received from the constant cycle setting device on the basis of the injection pretrigger signal timing generated by the timing control device, and generates the operation timing of the linear accelerator.

14. A charged particle irradiation system comprising:
a linear accelerator that operates in a predetermined operation cycle on the basis of a radiofrequency power supply for applying a pulse voltage for acceleration, and accelerates, at an operation timing based on the operation cycle, charged particles extracted from an ion source so as to causes a charged particle beam to be extracted from the linear accelerator;
a circular accelerator that operates in an operation cycle including a process of causing the charged particle beam to be injected into the circular accelerator, a process of accelerating the charged particle beam, a process of causing the charged particle beam to be extracted from the circular accelerator, and a process of decelerating the charged particle beam, causes the charged particle beam accelerated by the linear accelerator to be injected into the circular accelerator at a predetermined timing, accelerates the charged particle beam, and causes the accelerated charged particle beam to be extracted from the circular accelerator;
an irradiation device that radiates the charged particle beam extracted from the circular accelerator;
a first control device that controls an extractor of the circular accelerator in the process of causing the charged particle beam to be extracted from the circular accelerator in the operation cycle of the circular accelerator so that the charged particle beam is extracted from the circular accelerator only for a time period requested from the irradiation device; and
a second control device that changes the operation timing of the linear accelerator after the process of causing the charged particle beam to be extracted from the circular accelerator is completed by the control of the extractor in the operation cycle of the circular accelerator so that the operation cycle of the linear accelerator temporarily increases and the operation timing of the linear accelerator matches an injection timing of the next operation cycle of the circular accelerator.

15. A charged particle irradiation system comprising:
a linear accelerator that operates in a predetermined operation cycle on the basis of a radiofrequency power supply for applying a pulse voltage for acceleration, and accelerates, at an operation timing based on the operation cycle, charged particles extracted from an ion source so as to causes a charged particle beam to be extracted from the linear accelerator;
a circular accelerator that operates in an operation cycle including a process of causing the charged particle beam to be injected into the circular accelerator, a process of accelerating the charged particle beam, a process of causing the charged particle beam to be extracted from the circular accelerator, and a process of decelerating the charged particle beam, causes the charged particle beam accelerated by the linear accelerator to be injected into the circular accelerator at a predetermined timing, accelerates the charged particle beam, and causes the accelerated charged particle beam to be extracted from the circular accelerator;
an irradiation device that has a scanning magnet for deflecting the charged particle beam extracted from the circular accelerator so as to scan a target with the charged particle beam and irradiates the target with the charged particle beam that has passed through the scanning magnet;
a first control device that controls a excitation current to be applied to the scanning magnet, scans, with the charged particle beam, one of a plurality of layers, into which the target to be irradiated with the charged particle beam is divided in a depth direction, and outputs, after completion of the scanning of the one layer with the charged particle beam, an energy switch request indicating a request for a change in the energy of the charged particle beam to be extracted from the circular accelerator in order to scan another one of the layers with the charged particle beam; and
a second control device that changes the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches the injection timing of the next operation cycle of the circular accelerator in order to change the operation cycle of the circular accelerator to the next operation cycle on the basis of the energy switch request.

16. A charged particle irradiation system comprising:
a linear accelerator that operates in a predetermined operation cycle on the basis of a radiofrequency power supply for applying a pulse voltage for acceleration, and accelerates, at an operation timing based on the operation cycle, charged particles extracted from an ion source so as to causes a charged particle beam to be extracted from the linear accelerator;
a circular accelerator that operates in an operation cycle including a process of causing the charged particle beam to be injected into the circular accelerator, a process of accelerating the charged particle beam, a process of causing the charged particle beam to be extracted from the circular accelerator and a process of decelerating the charged particle beam, causes the charged particle beam accelerated by the linear accelerator to be injected into the circular accelerator at a predetermined timing, accelerates the charged particle beam, and causes the accelerated charged particle beam to be extracted from the circular accelerator;
an irradiation device that has a scanning magnet for deflecting the charged particle beam extracted from the circular accelerator so as to scan a target with the charged particle beam and irradiates the target with the charged particle beam that has passed through the scanning magnet;
a first control device that controls an excitation current to be applied to the scanning magnet and scans the target with the charged particle beam, and that stops the process of causing the charged particle beam to be extracted from the circular accelerator in the operation cycle of the circular accelerator and outputs an operational pattern transition request indicating a request for a transition to an operational pattern of the next operation cycle when charged particles that are stored in the circular accelerator are depleted during the scanning with the charged particle beam or when a time for irradiation that can be performed during one cycle of the circular accelerator is not sufficient and elapses during the scanning with the charged particle beam; and
a second control device that changes the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches the injection timing of the next operation cycle of the circular accelerator in order to change the operation cycle of the circular accelerator to the next operation cycle on the basis of the operational pattern transition request.

17. A charged particle irradiation system comprising:

a linear accelerator that operates in a predetermined operation cycle on the basis of a radiofrequency power supply for applying a pulse voltage for acceleration, and accelerates, at an operation timing based on the operation cycle, charged particles extracted from an ion source so as to causes a charged particle beam to be extracted from the linear accelerator;

a circular accelerator that operates in an operation cycle including a process of causing the charged particle beam to be injected into the circular accelerator, a process of accelerating the charged particle beam, a process of causing the charged particle beam to be extracted from the circular accelerator, and a process of decelerating the charged particle beam, causes the charged particle beam accelerated by the linear accelerator to be injected into the circular accelerator at a predetermined timing, accelerates the charged particle beam, and causes the accelerated charged particle beam to be extracted from the circular accelerator;

an irradiation device that temporally or spatially forms the charged particle beam extracted from the circular accelerator and irradiates a target with the charged particle beam so that the shape of the target matches a region to be irradiated with the charged particle beam;

a first control device that sets, on the basis of a signal obtained by a detection of a movement of the target to be irradiated, a timing of a time period for which the target can be irradiated, and that outputs a beam request indicating a request to extract the charged particle beam only for the time period for which the target can be irradiated; and a second control device that changes the operation timing of the linear accelerator after completion of the process of causing the charged particle beam to be extracted from the circular accelerator in the operation cycle of the circular accelerator so that the operation cycle of the linear accelerator temporarily increases and the operation timing of the linear accelerator matches an injection timing of the next operation cycle of the circular accelerator in order to change the operation cycle of the circular accelerator to the next operation cycle on the basis of the beam request.

18. The charged particle irradiation system according to claim 14, wherein the second control device sets the timing signal so that a time period that ranges from the time of the generation of the timing signal to the injection timing of the next operation cycle of the circular accelerator is equal to an integral multiple of the operation cycle of the linear accelerator, and wherein the second control device generates the operation timing of the linear accelerator when one operation cycle of the linear accelerator elapses after the generation of the timing signal.

19. The charged particle irradiation system according to claim 14, wherein the second control device sets the timing signal so that a time period that ranges from the time of the generation of the timing signal to the injection timing of the next operation cycle of the circular accelerator is equal to the sum of an integral multiple of the operation cycle of the linear accelerator and a certain time period that is shorter than the operation cycle of the linear accelerator, wherein when the operation timing of the linear accelerator is immediately before the generation of the timing signal, and the sum of the certain time period and a time period ranging from the operation timing of the linear accelerator to the time of the generation of the timing signal is larger than one operation cycle of the linear accelerator, the second control device generates the operation timing of the linear accelerator when the certain time period elapses after the generation of the timing signal, and wherein when the operation timing of the linear accelerator is immediately before the generation of the timing signal, and the sum of the certain time period and the time period ranging from the operation timing of the linear accelerator to the time of the generation of the timing signal is not larger than one operation cycle of the linear accelerator, the second control device generates the operation timing of the linear accelerator when the sum of one operation cycle of the linear accelerator and the certain time period elapses after the generation of the timing signal.

* * * * *